(12) United States Patent
Hasan et al.

(10) Patent No.: US 7,175,608 B2
(45) Date of Patent: Feb. 13, 2007

(54) DEVICE FOR THE IDENTIFICATION OF THE EPIDURAL SPACE

(76) Inventors: Maan Hasan, 18 Kenelm Close, Harrow, Middlesex (GB) HA1 3TE; Jim Roberts, 309 A Shirland Road, London (GB) W9 3JL ( * ) Notice: Subject to any disclaimer, the term of this patent is extended or adjusted under 35 U.S.C. 154(b) by 96 days.

(21) Appl. No.: 10/394,503

(22) Filed: Mar. 20, 2003

(65) Prior Publication Data

US 2004/0186430 A1  Sep. 23, 2004

(51) Int. Cl.
*A61M 5/00* (2006.01)
(52) U.S. Cl. .................................................. 604/117
(58) Field of Classification Search ............ 604/96.01, 604/117, 523, 319, 118; 600/485, 486
See application file for complete search history.

(56) References Cited

U.S. PATENT DOCUMENTS

| | | | | |
|---|---|---|---|---|
| 4,000,741 A | * | 1/1977 | Binard et al. ............... | 604/121 |
| 4,108,175 A | * | 8/1978 | Orton .................... | 604/168.01 |
| 4,215,699 A | | 8/1980 | Patel ......................... | 128/748 |
| 4,414,983 A | * | 11/1983 | Evans et al. ................ | 600/560 |
| 4,535,773 A | * | 8/1985 | Yoon .......................... | 606/185 |
| 4,664,660 A | * | 5/1987 | Goldberg et al. ........... | 604/321 |
| 4,801,293 A | * | 1/1989 | Jackson ...................... | 604/505 |
| 4,817,629 A | * | 4/1989 | Davis et al. ................. | 600/561 |
| 5,188,594 A | * | 2/1993 | Zilberstein .................. | 604/506 |
| 5,258,003 A | | 11/1993 | Ciaglia et al. .............. | 606/185 |
| 5,261,883 A | * | 11/1993 | Hood et al. ................. | 604/153 |
| 5,267,964 A | * | 12/1993 | Karg ........................... | 604/141 |
| 5,387,188 A | * | 2/1995 | Watson .......................... | 604/8 |
| 5,725,509 A | * | 3/1998 | Scarfone et al. ............ | 604/217 |
| 5,902,273 A | * | 5/1999 | Yang et al. ................. | 604/118 |
| 6,773,417 B2 | * | 8/2004 | Fitzgibbons et al. ........ | 604/118 |

FOREIGN PATENT DOCUMENTS

EP  0091846 A1  10/1983
EP  0538259 A1  4/1993

OTHER PUBLICATIONS

Search Report for GB 0016399.8 (Search dated Jan. 9, 2002).

* cited by examiner

*Primary Examiner*—Sharon Kennedy
(74) *Attorney, Agent, or Firm*—Kirkpatrick & Lockhart Nicholson Graham, LLP

(57) ABSTRACT

The invention provides devices and methods for identification of an epidural space. The invention also provides for visually determining when a needle enters the epidural space.

12 Claims, 3 Drawing Sheets

DEVICE FOR THE IDENTIFICATION OF THE EPIDURAL SPACE

TECHNICAL FIELD

The present invention relates to a device that aids injection into an epidural space.

BACKGROUND INFORMATION

In medical practice, identification of the epidural space is required for therapeutic and anesthetic procedures.

The currently used techniques rely on high levels of manual skill and dexterity and require specialist training. These techniques are commonly associated with technical difficulties or complications. For example, trainees have a high complication rate that decreases with experience. In fact, it can take up to 2 years to learn the techniques involved to identify the epidural space. The current techniques rely on a kinetic "feel" endpoint.

DESCRIPTION OF THE INVENTION

The invention generally relates to an injection device that aids injection into an epidural space. This device allows a user to identify and clearly visualise when a needle enters the epidural space or cavity.

Devices according to the invention include a diaphragm that is adapted for pressurization. The diaphragm bulges outwards when the device is pressurized. Also, the device is adapted to connect to a needle. In some embodiments, the device is device is pressurized with air or saline. Also in some embodiments, the device includes an injection port for injection of pressurizing fluid.

In some embodiments, the device incorporates a connection port for connecting to a needle. In some embodiments, a needle is an epidural needle. Devices according to the invention can be used in medicine.

The invention also includes methods of injection into a body cavity of a patient, which has an internal pressure less than atmospheric pressure, that include the steps of: attaching a device described herein to a needle; pressurizing the device with a fluid until the diaphragm bulges outwards; and advancing the needle into a patient until the diaphragm retracts.

An object of this invention is to provide the operator of this procedure with a device that achieves a high success rate, a steep training/learning curve, and a minimal complication rate.

Several devices to aid in the detection of the epidural space have been described previously. Some of these devices use the feature of low pressure in the epidural space to identify when the needle enters the space. European Patent No. EP0091846 and U.S. Pat. No. 5,188,594 both describe devices that contain a balloon, which is inflated prior to the needle entering the epidural space. As the pressure within the epidural space is lowered, the balloon deflates when the needle enters the epidural space. This results in the air being injected into the epidural space, which can cause unwanted side effects, such as air bubbles that form and prevent the even spread of the medication administered.

European Patent No. 0538259 discloses an electronic means of detecting changes in pressure within the liquid inside the syringe, and can provide a visual and/or aural end point. However, the device disclosed therein increases the length of the equipment used, which provides a larger axis of movement. Furthermore, this also makes the device cumbersome, thus often requiring the operator to have one hand on the needle. In addition, the electronic equipment used with such devices needs to be calibrated and is prone to failure.

U.S. Pat. Nos. 5,902,273 and 5,258,003 describe devices that make use of a spring-loaded mechanical gauge to indicate the loss in pressure. These gauges are not well suited for detecting the low pressures encountered during the insertion of an epidural needle. In practice, these devices failed due to the complexity of the device, mechanical stickiness and also the increase in weight.

U.S. Pat. No. 4,215,699 discloses a device that incorporates a membrane, which is displaced inwardly or outwardly in response to a decrease or increase in pressure respectively. This device, however, cannot detect small pressure changes.

Therefore, a small, simple and lightweight device that clearly indicates when a needle enters the epidural space is needed to improve epidural injection techniques.

Thus in one aspect, the present invention provides an injection device including a diaphragm that is adapted for pressurization, so that the diaphragm bulges outwards when the device is pressurized, and wherein the device is adapted to connect to a needle.

The term "adapted for pressurization" as used herein means that the device can be pressurized prior to use, so that the diaphragm bulges outwards. This provides a visual indication of when the needle enters a space which has a lower pressure, such as the epidural cavity.

The device can be pressurized with a fluid. The term "fluid" as used herein refers to a gas or a liquid. In some preferred embodiments the fluid is saline or air.

In another preferred embodiment, the device is adapted for connection to the needle by means of a connection port. In another embodiment, the device further includes an injection port for the injection of pressurizing fluid.

The device can be adapted for pressurization by the presence of one or more valves. A valve, in particular a one way valve, may be present in the injection port, so that the pressure is maintained until the tip of the needle enters an area of low pressure within the body, such as the epidural space.

The means for connecting the device to the needle may also contain a valve. The valve can be closed to enable the device to be pressurized. Once the device is connected to the needle, and the needle has been inserted into the body, the valve can be opened so that any decrease in pressure experienced at the tip of the needle is detected by the retraction of the diaphragm.

In one preferred embodiment the needle is an epidural needle.

The invention provides for pressurization of the device and automatic injection of a fluid (air or saline) at the point of entry to the epidural space. However, in comparison to the balloon devices described in European Patent No. 0091846 and U.S. Pat. No. 5,188,594, a greater and more accurate displacement of the membrane is achieved with a smaller volume of air entering the epidural space. As a result, this causes less side effects. Alternatively, the use of a fluid such as saline to pressurize the chamber eliminates the problem of the introduction of air into the epidural space.

The present device provides an instant clear visual aid for identification of the point of entry into the epidural space. The invention provides for full concentration and undivided attention of the operator on the advancement of the epidural needle. It also frees her or his hands thereby allowing for a bi-manual grip of the epidural needle wings and a steady control on its movement. Previous devices generally have only allowed one hand to be used, which in combination with lengthy apparatus causes an undesirably large axis of movement.

Furthermore due to the design of the device, it can be easily made by injection moulding.

In another aspect the present invention, the device provides for the use of an injection device as described herein for use in medicine.

In a further aspect, the present invention provides a method of injection into a body cavity of a patient which has an internal pressure less than atmospheric pressure comprising the following steps:
 a) attaching an injection device as defined herein to a needle;
 b) pressurizing the device with a fluid until the diaphragm bulges outwards; and,
 c) advancing the needle into a patient until the diaphragm retracts.

In some embodiments, devices according to the invention that connect to the epidural needle include a diaphragm on one side that bulges when pressurized by injection of air or saline, and retracts when the pressure is lost on entering an epidural space. In some embodiments, devices have an integral one-way valve for the injection of air or saline. Moreover, in some embodiments, a device includes an injection port for injecting air or saline and a connection port for connecting to a needle, such as an epidural needle.

DESCRIPTION OF THE DRAWINGS

The invention will now be described with reference to the accompanying drawings. In the drawings, like reference characters generally refer to the same parts throughout the different views. Also, the drawings are not necessarily drawn to scale, emphasis instead generally being placed upon illustrating the principles of the invention.

Figure 1:
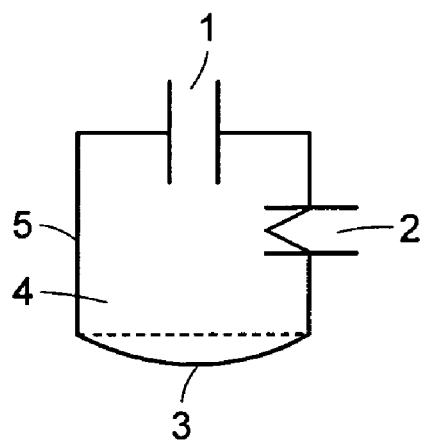
FIG. 1 shows a line-draw view from the side of an embodiment of the invention.
Figure 2:
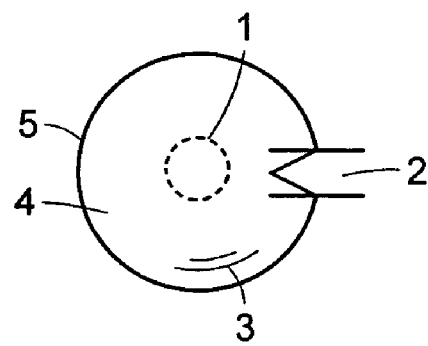
FIG. 2 shows a line-draw view from the front of an embodiment of the invention.
Figure 3:
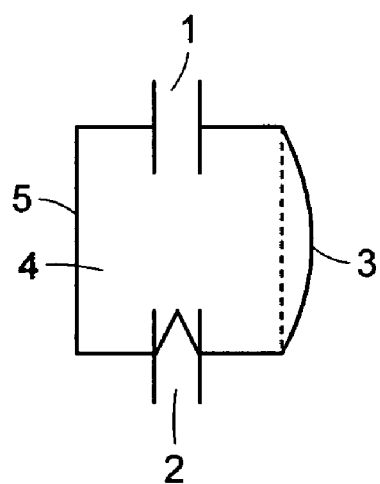
FIG. 3 shows a line-draw view from the side of an alternative embodiment of the invention.

The body of a device 5 is connected to the epidural needle via end 1. End 2 is the injection port through which the fluid can be injected to pressurize the cavity. It incorporates a one-way valve which may be made of, for example, flaps of elastic material such as rubber (two flaps are shown in FIGS. 1, 2, and 3.) The elastic diaphragm 3 is designed to bulge outwardly when the cavity 4 is pressurized by a fluid, for example air or saline. The diaphragm 3 flattens when the pressure is lost suddenly, for example when the needle enters the epidural space, providing a visual end point. This diaphragm 3 may be made of thin elastic material such as rubber or other imitative synthetic fiber. The cavity 4, which could have different shapes such as cylindrical or cubical, may be pressurized by injection of air or saline. The body of the device 5, excluding the diaphragm 3 and the valve, can be made of hard material for example plastic.

Figure 4:
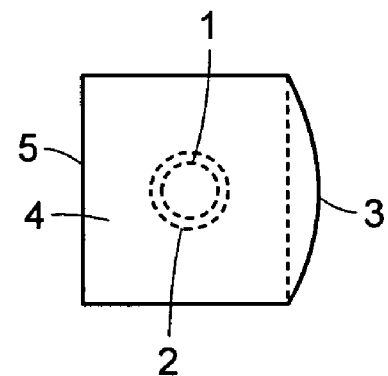
FIG. 4 shows a line-draw view from the front of an alternative embodiment of the invention.
Figure 5A:
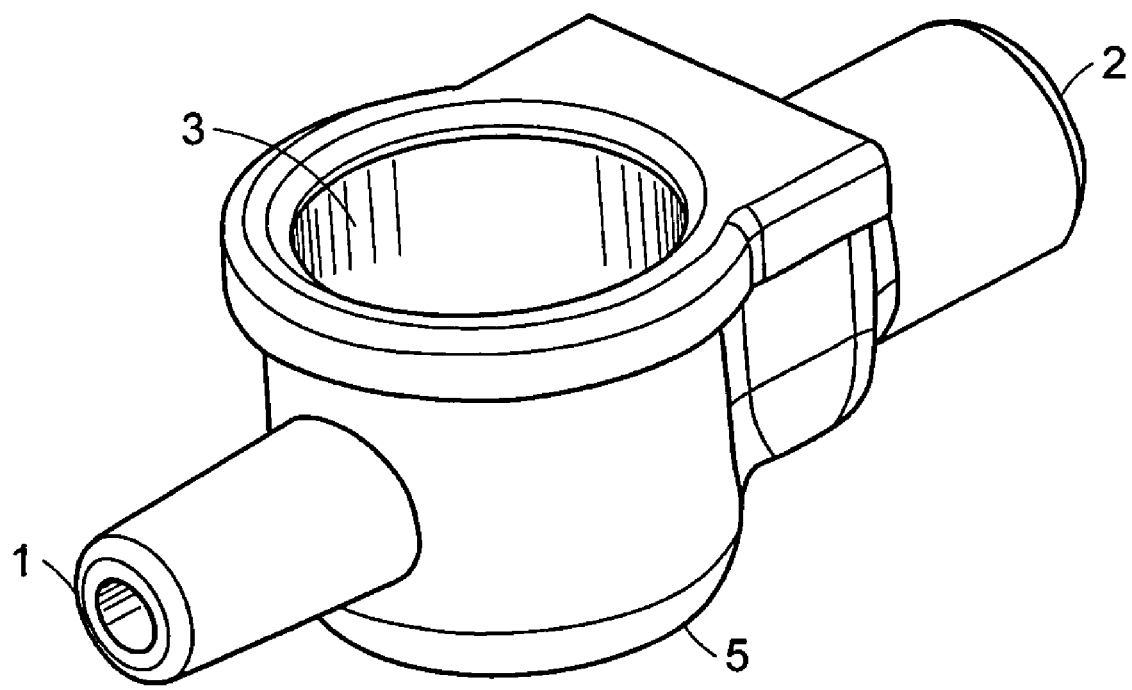
FIG. 5a shows a right, side-perspective of an embodiment of the invention.
Figure 5B:
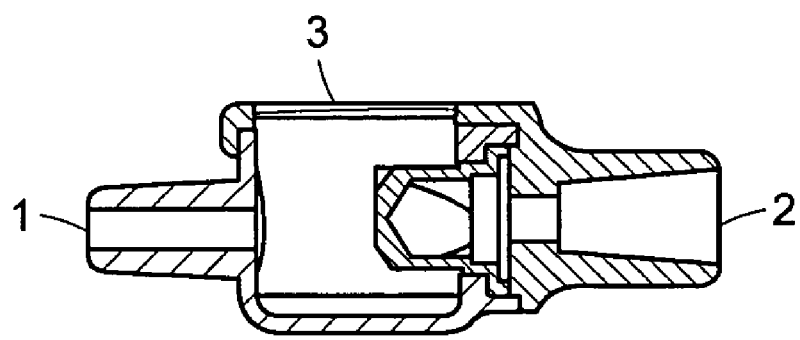
FIG. 5b shows a cross section through an embodiment of the device, which shows a valve at the end of the injection port.
Figure 6:
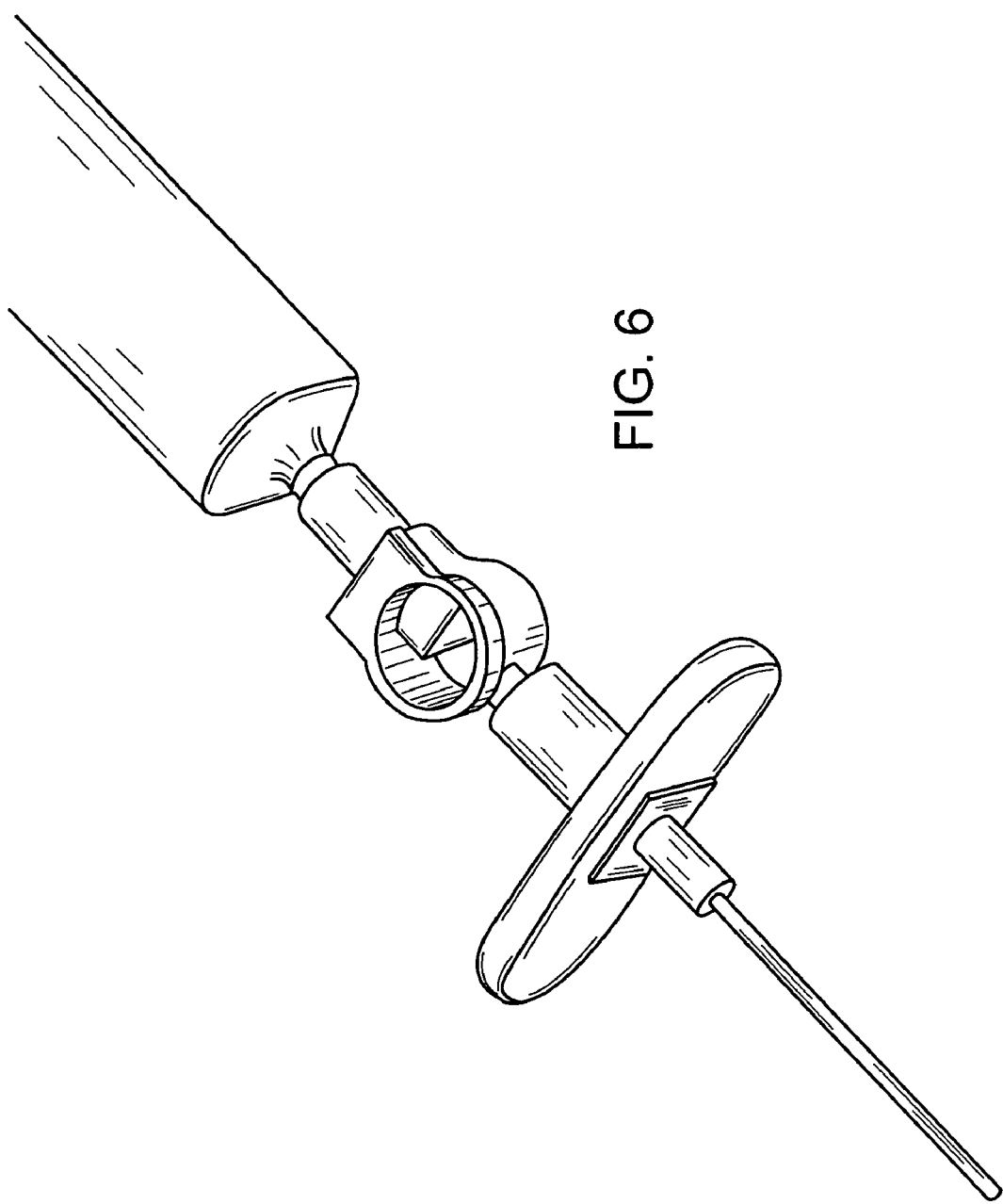
FIG. 6 show an embodiment of the invention in use, and attached to a needle and a syringe.

The same components of this invention may be rearranged in an alternative design such as shown in the side and front line-draw views of FIGS. 3 and 4 respectively.

All features of each of the aspects of the present invention apply to all other aspects mutatis mutandis. Variations, modifications, and other implementations of what is described herein will occur to those of ordinary skill in the art without departing from the spirit and the scope of the invention as claimed. Accordingly, the invention is to be defined not by the preceding illustrative embodiments but instead by the spirit and scope of the following claims.

U.K. Application No. GB2366729 also discloses devices and methods for identifying an epidural space, and is incorporated by reference herein. Furthermore, each of the patent documents disclosed hereinabove is incorporated by reference herein.

We claim:

1. A device that indicates when a needle enters an epidural space comprising:
 a rigid body having a diaphragm on one side, adapted for pressurization, so that said diaphragm bulges outwards to visually indicate when the device is pressurized, and a one-way valve adapted to maintain pressurization, wherein said device is adapted to connect to an epidural needle.

2. The device of claim 1 wherein the device is pressurized with air or saline.

3. The device of claim 1 wherein said device further incorporates a connection port for connecting to the needle.

4. The device of claim 1 further comprising an injection port for injection of pressurized fluid.

5. The use of the device of claim 1 for identifying the epidural space comprising the following steps:
 a) attaching said device to an epidural needle;
 b) pressurizing the device with a fluid until a diaphragm on the device bulges outwards; and
 c) advancing the epidural needle into a patient until the diaphragm retracts.

6. The device of claim 1 wherein the one-way valve comprises two flaps, each flap comprising an elastic material.

7. The device of claim 1 further comprising an injection port connected to the one-way valve, the injection port adapted to receive a pressurizing fluid from a syringe, the one-way valve adapted to maintain diaphragm inflation after removal of the syringe.

8. The device of claim 1 wherein the diaphragm is adapted to bulge outwards until the tip of the needle enters an area within a patient wherein a pressure of the area is lower than a pressure in the device.

9. The device of claim 3 wherein the device includes a second one-way valve in fluid communication with the connection port.

10. The device of claim 4 wherein the one-way valve is connected to the injection port.

11. A method of injection into an epidural space comprising the following steps:
 a) attaching an injection device to an epidural needle;
 b) pressurizing the device with a fluid until a diaphragm on the device bulges outwards;
 c) preventing fluid release from the device with a one-way valve; and
 d) advancing the needle into a patient until the diaphragm retracts.

12. The method of claim 11, wherein the step of pressurizing the device with a fluid further comprises the steps of attaching a syringe to the injection device, and injecting fluid from the syringe into the device.

* * * * *